(12) United States Patent
Van Kruchten (10) Patent No.: US 8,063,256 B2
(45) Date of Patent: *Nov. 22, 2011

(54) PROCESS FOR THE PREPARATION OF ALKYLENE GLYCOL

(75) Inventor: Eugene Marie Godfried Andre Van Kruchten, Amsterdam (NL)

(73) Assignee: Shell Oil Company, Houston, TX (US)

( * ) Notice: Subject to any disclaimer, the term of this patent is extended or adjusted under 35 U.S.C. 154(b) by 440 days.

This patent is subject to a terminal disclaimer.

(21) Appl. No.: 12/269,818

(22) Filed: Nov. 12, 2008

(65) Prior Publication Data

US 2009/0156867 A1    Jun. 18, 2009

(30) Foreign Application Priority Data

Nov. 14, 2007    (EP) ..................................... 07120666

(51) Int. Cl.
    *C07C 29/50*    (2006.01)
(52) U.S. Cl. ....................................... 568/910
(58) Field of Classification Search .................... 568/910
    See application file for complete search history.

(56) References Cited

U.S. PATENT DOCUMENTS 5,218,135 A    6/1993    Buysch et al. ................ 558/277

FOREIGN PATENT DOCUMENTS

| EP | 024628 | 3/1981 |
| EP | 776890 | 6/1997 |
| GB | 2107712 | 5/1983 |

*Primary Examiner* — Sikarl Witherspoon (57) ABSTRACT

The invention provides a process for the preparation of an alkylene glycol from an alkene. The gas composition from an alkylene oxide reactor is contacted with lean absorbent in an alkylene oxide absorber in the presence of one or more catalysts that promote carboxylation. The lean absorbent comprises at least 50 wt % alkylene carbonate and less than 10 wt % water and is supplied to the alkylene oxide absorber at a temperature greater than 60° C. Alkylene oxide reacts with carbon dioxide in the absorber, forming alkylene carbonate, and fat absorbent comprising alkylene carbonate is withdrawn from the absorber. A portion of the fat absorbent is supplied to one or more hydrolysis reactors, wherein alkylene carbonate reacts with water in the presence of one or more hydrolysis catalysts. The product stream from the hydrolysis reactor is dehydrated and purified.

13 Claims, 6 Drawing Sheets

PROCESS FOR THE PREPARATION OF ALKYLENE GLYCOL

This application claims the benefit of European Application No. 07120666.8 filed Nov. 14, 2007.

FIELD OF THE INVENTION

The present invention relates to a process for the preparation of an alkylene glycol from an alkene.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol is typically prepared from ethylene oxide, which is in turn prepared from ethylene. Ethylene and oxygen are passed over a silver oxide catalyst, typically at pressures of 10-30 bar and temperatures of 200-300° C., producing a product stream comprising ethylene oxide, carbon dioxide, ethylene, oxygen and water. The amount of ethylene oxide in the product stream is usually between about 0.5 and 10 weight percent. The product stream is supplied to an ethylene oxide absorber and the ethylene oxide is absorbed by a recirculating solvent stream containing mostly water. The ethylene oxide-depleted stream is partially or entirely supplied to a carbon dioxide absorption column wherein the carbon dioxide is at least partially absorbed by a recirculating absorbent stream. Gases that are not absorbed by the recirculating absorbent stream are recombined with any gases bypassing the carbon dioxide absorption column and are recycled to the ethylene oxide reactor.

The solvent stream leaving the ethylene oxide absorber is referred to as fat absorbent. The fat absorbent is supplied to an ethylene oxide stripper, wherein ethylene oxide is removed from the fat absorbent as a vapour stream. The ethylene oxide-depleted solvent stream is referred to as lean absorbent and is recirculated to the ethylene oxide absorber to absorb further ethylene oxide.

The ethylene oxide obtained from the ethylene oxide stripper can be purified for storage and sale or can be further reacted to provide ethylene glycol. In one well-known process, ethylene oxide is reacted with a large excess of water in a non-catalytic process. This reaction typically produces a glycol product stream consisting of almost 90 weight percent monoethylene glycol, the remainder being predominantly diethylene glycol, some triethylene glycol and a small amount of higher homologues. In another well-known process, ethylene oxide is catalytically reacted with carbon dioxide to produce ethylene carbonate. The ethylene carbonate is subsequently hydrolysed to provide ethylene glycol. Reaction via ethylene carbonate significantly improves the selectivity of ethylene oxide conversion to monoethylene glycol.

The lean absorbent that is supplied to the ethylene oxide absorber is typically aqueous, but in the process disclosed in EP 24 628 the lean absorbent is ethylene carbonate. The fat absorbent, containing ethylene oxide and carbon dioxide dissolved in ethylene carbonate, is sent to a stripper wherein ethylene oxide and carbon dioxide are stripped, and ethylene carbonate is returned as lean absorbent to the ethylene oxide absorber. The stripped ethylene oxide and carbon dioxide are supplied to an ethylene carbonate reactor and react to ethylene carbonate in the presence of an anion-exchange resin, functioning as a carboxylation catalyst.

EP 776 890 discloses a similar process. The lean absorbent that is supplied to the ethylene oxide absorber mainly contains ethylene carbonate and ethylene glycol. The fat absorbent, containing ethylene oxide and carbon dioxide dissolved in ethylene carbonate and ethylene glycol, is supplied directly to an ethylene carbonate reactor wherein ethylene oxide and carbon dioxide react in the presence of a catalyst. The absorption apparatus is operated at low temperature and carboxylation occurs in a subsequent reactor wherein the conditions promote carboxylation.

GB 2 107 712 discloses an alternative process where the gases from an ethylene oxide reactor are supplied directly to a reactor wherein ethylene oxide is converted to ethylene carbonate in the presence of a carboxylation catalyst.

The present inventors have sought to further improve the manufacture of alkylene glycol from an alkene and in particular have sought to provide a process that reduces the complexity (and reduces the cost) of the plant whilst ensuring high selectivity.

SUMMARY OF THE INVENTION

Accordingly, the present invention provides a process for the preparation of an alkylene glycol from an alkene comprising steps of:

(a) reacting the alkene with oxygen in the presence of a catalyst in a reactor to produce a gas composition comprising alkylene oxide, alkene, oxygen, carbon dioxide and water vapour;

(b) removing water from the gas composition;

(c) supplying the gas composition from (b) to an alkylene oxide absorber, supplying lean absorbent to the alkylene oxide absorber, contacting the gas composition with lean absorbent in the alkylene oxide absorber in the presence of one or more catalysts that promote carboxylation, and withdrawing fat absorbent from the absorber, wherein the lean absorbent comprises at least 50 wt % alkylene carbonate and comprises less than 10 wt % water, and wherein the lean absorbent is supplied at a temperature greater than 60° C.;

(d) supplying a portion of the fat absorbent from step (c) to one or more hydrolysis reactors, supplying water to the one or more hydrolysis reactors, contacting the fat absorbent with water in the presence of one or more hydrolysis catalysts in the one or more hydrolysis reactors, and withdrawing a product stream from the one or more hydrolysis reactors;

(e) supplying the product stream from step (d) to a dehydrator, removing water and providing a dehydrated product stream; and (f) purifying the dehydrated product stream from step (e) and providing a purified alkylene glycol product stream.

In the process of the invention, the alkylene oxide absorber acts both as an absorber, absorbing alkylene oxide from the gas composition, and as a reactor, converting alkylene oxide to alkylene carbonate. Supplying a carboxylation catalyst and lean absorbent at a temperature of at least 60° C. to the alkylene oxide absorber promotes carboxylation in the alkylene oxide absorber, and there is significant conversion of alkylene oxide to alkylene carbonate in the absorber. Water is removed from the gas composition before it is supplied to the alkylene oxide absorber and the lean absorbent comprises at least 50 wt % alkylene carbonate and less than 10 wt % water. By restricting the amount of water supplied to the alkylene oxide absorber, there is a reduced requirement to remove water from any gases that are recirculated from the alkylene oxide absorber to the alkylene oxide reactor, and there is more opportunity to use carboxylation catalysts that function most effectively in substantially non-aqueous environments.

DETAILED DESCRIPTION OF THE INVENTION

The present invention provides a process for the preparation of an alkylene glycol from an alkene, via an alkylene oxide and an alkylene carbonate:

$R^1$, $R^2$, $R^3$ and $R^4$ are preferably chosen from hydrogen or an optionally substituted alkyl group having from 1 to 6 carbon atoms, more preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted $C_1$-$C_3$-alkyl group and, more preferably, $R^1$, $R^2$, $R^3$ and $R^4$ all represent hydrogen atoms.

Examples of suitable alkenes therefore include ethylene and propylene. In the present invention the most preferred alkene is ethylene.

The alkene is reacted with oxygen in the presence of a catalyst in a reactor to produce a gas composition comprising alkylene oxide, alkene, oxygen, carbon dioxide and water vapour. The oxygen may be supplied as oxygen or as air, but is preferably supplied as oxygen. Ballast gas, for example methane or nitrogen, is typically supplied to allow operation at high oxygen levels without causing a flammable mixture. Moderator, e.g. monochloroethane or dichloroethane, may be supplied for ethylene oxide catalyst performance control. The alkene, oxygen, ballast gas and moderator are preferably supplied to recycle gas that is supplied to the alkylene oxide reactor from the alkylene oxide absorber (optionally via a carbon dioxide absorption column).

The alkylene oxide reactor is typically a multitubular, fixed bed reactor. The catalyst is preferably finely dispersed silver and optionally promoter metals on a support material, for example, alumina. The reaction is preferably carried out at pressures of greater than 1 MPa and less than 3 MPa and temperatures of greater than 200° C. and less than 300° C. The gas composition from the alkylene oxide reactor is preferably cooled in one or more coolers, preferably with generation of steam at one or more temperature levels.

Water is removed from the gas composition before it is supplied to the alkylene oxide absorber. Additionally, contaminants are preferably removed from the gas composition before it is supplied to the alkylene oxide absorber. Possible contaminants include acids, esters, aldehydes, acetals and organic halides.

A preferred method of removing water and optionally contaminants is quenching, preferably by contacting the gas composition with a recirculating aqueous solution, that is preferably cooled or chilled, e.g. less than 20° C. Lowering the quench temperature will reduce the water content in the gas feed to the alkylene oxide absorber. Quenching is preferably carried out in the same vessel as the alkylene oxide absorber. A portion of the recirculating aqueous solution may be withdrawn as a bleed stream from the quench section, and any alkylene oxide in the bleed stream may be recovered by conventional methods. In one embodiment, substances, e.g. bases such as sodium hydroxide, are added to the recirculating aqueous solution to enhance removal of contaminants. After quenching the gas composition may be reheated before it is supplied to the alkylene oxide absorber, preferably by heat integration with the hot gas composition emerging from the alkylene oxide reactor.

Another method of removing water and optionally contaminants is to cool the gas stream using heat exchangers, causing condensation of water that can thereafter be removed. Most preferably water and optionally contaminants are removed using both quenching and cooling by heat exchangers. If the water content in the gas to the alkylene oxide absorber remains high, the water content in the absorber may optionally be reduced by supplying hydrolysis catalyst to the alkylene oxide absorber (and/or to any finishing reactor(s)), thereby promoting reaction of any water that is present with alkylene oxide to form alkylene glycol.

The gas composition from step (b) is supplied to an alkylene oxide absorber. The alkylene oxide absorber preferably comprises a column of vertically stacked trays or a packed column. The trays or the packed column provide a surface area for the absorbent and gas composition to come into contact, facilitating mass transfer between the two phases. Additionally, trays provide considerable liquid volume in which the liquid phase reaction can occur. In the embodiment wherein the alkylene oxide absorber comprises a series of vertically stacked trays, gases can pass upwards through the trays and liquid can flow downwards from tray to tray. Preferably the column comprises at least 20 trays, more preferably at least 30 trays. Preferably the column comprises less than 70 trays. More trays increase the absorption ability and reaction volume of the column, but adding additional trays increases expense. In the embodiment wherein the alkylene oxide absorber comprises a packed column, conventional packing such as structured packing, random packing and catalytic distillation internals may be used.

The gas composition from step (b) is preferably supplied at the bottom of the alkylene oxide absorber. If the alkylene oxide absorber comprises a column of vertically stacked trays, the gas composition is preferably supplied below the bottom tray in the column. If the alkylene oxide absorber comprises a packed column, the gas composition is preferably supplied below the packing material.

Lean absorbent is supplied to the alkylene oxide absorber and contacted with the gas composition in the alkylene oxide absorber and fat absorbent (comprising components absorbed from the gas composition including alkylene carbonate) is withdrawn from the alkylene oxide absorber. In one embodiment, the lean absorbent is supplied at the top of the alkylene oxide absorber. If the alkylene oxide absorber comprises a column of vertically stacked trays, the lean absorbent is preferably supplied to the uppermost tray in the absorption column. If the alkylene oxide absorber comprises a packed column, the lean absorbent is preferably supplied above the packing material. In another embodiment, the lean absorbent is supplied such that there are trays or packing above the point at which the lean absorbent is supplied to the alkylene oxide absorber. In this embodiment, additional lean absorbent that has been cooled can be supplied at the top of the alkylene oxide absorber to absorb alkylene oxide or contaminants in the top of the alkylene oxide absorber.

The lean absorbent comprises at least 50 wt % alkylene carbonate and comprises less than 10 wt % water. If the process of the invention is for the preparation of ethylene glycol, the preferred alkylene carbonate is ethylene carbonate. If the process of the invention is for the preparation of propylene glycol, the preferred alkylene carbonate is propylene carbonate. The lean absorbent preferably comprises at least 60 wt % alkylene carbonate and more preferably comprises at least 70 wt % alkylene carbonate. The lean absorbent preferably comprises less than 3 wt % water and more preferably comprises less than 2 wt % water. Minimising the amount of water is particularly important if the carboxylation catalyst is water sensitive. The lean absorbent may also comprise alkylene glycol.

The gas composition is contacted with lean absorbent in the alkylene oxide absorber in the presence of one or more catalysts that promote carboxylation. In one embodiment of the invention, the one or more catalysts that promote carboxylation is/are homogeneous, and the lean absorbent comprises the one or more catalysts. Homogeneous catalysts that are known to promote carboxylation in substantially non-aqueous media include combinations of zinc halides (especially zinc iodide and zinc bromide) with quaternary ammonium or phosphonium halides (for example n-butyl ammonium halides), ionic liquids such as imidazolium salts, pyridine derivatives, indium halides, lead halides and polyoxometalates. Other homogeneous carboxylation catalysts known to the skilled person include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. In another embodiment of the invention, the one or more catalysts that promote carboxylation is/are heterogeneous. The heterogeneous catalyst(s) are preferably contained in vertically stacked trays or in the packing of a packed column. Heterogeneous catalysts that promote carboxylation are preferably based upon solid supports such as ion exchange resins, silica, polysiloxane, polyvinylpyridine or polystyrene. Preferably a solid support such as an ion exchange resin is functionalised with a quaternary ammonium or phosphonium halide and is used in combination with a metal salt co-catalyst such as a zinc halide. Alternatively quaternary ammonium and quaternary phosphonium halides may be immobilized on silica or bound to insoluble polystyrene beads. Alternatively metal salts such as zinc halides may be supported on solid supports such as polyvinylpyridine, polyvinylpyrrolidine and chitosan. The heterogeneous catalyst is preferably integrated into the absorber using reactive distillation packing such as M-Series™ packing from CDTech, Katapak™ SP packing from Sulzer Chemtech, Katamax™ packing from Koch or Multipak™ packing from Montz.

The most preferred catalyst will have high activity for the carboxylation reaction when present in a reaction medium consisting predominantly of alkylene carbonate and comprising very little water. The catalyst will preferably be stable during the reaction and not be prone to leaching or degradation due to impurities.

The lean absorbent is supplied to the alkylene oxide absorber at a temperature greater than 60° C. Supplying the lean absorbent at a temperature greater than 60° C. promotes carboxylation in the absorber and ensures that the alkylene carbonate that is produced does not solidify. Solidification is a common problem for ethylene carbonate, which has a melting point of 34° C. Preferably the lean absorbent is supplied at a temperature greater than 65° C., more preferably at a temperature greater than 70° C., even more preferably at a temperature greater than 80° C. and most preferably at a temperature between 90° C. and 250° C.

The gas composition from (a) is preferably supplied to the alkylene oxide absorber at a temperature greater than 60° C. Preferably the gas composition is supplied at a temperature greater than 65° C., more preferably at a temperature greater than 70° C., even more preferably at a temperature greater than 80° C. and most preferably at a temperature between 90° C. and 200° C.

The temperature in the alkylene oxide absorber is affected by the temperature of the gas composition and lean absorbent supplied to the alkylene oxide absorber. Additionally, because the carboxylation reaction is exothermic, it is preferred to control the temperature in the alkylene oxide absorber by withdrawing absorbent from the column, cooling and returning the absorbent to the column. The temperature in the alkylene oxide absorber is preferably controlled such that it is greater than 80° C., more preferably greater than 90° C. and is preferably less than 250° C. This temperature promotes the carboxylation reaction and ensures that the alkylene carbonate that is produced does not solidify.

The pressure in the alkylene oxide absorber is preferably from 1 to 4M Pa, more preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

The alkylene oxide and carbon dioxide in the gas composition from step (b) are absorbed into the absorbent. The carboxylation catalyst promotes carboxylation and preferably at least 60% of the alkylene oxide entering the alkylene oxide absorber is converted to alkylene carbonate in the alkylene oxide absorber. More preferably at least 80% of the alkylene oxide entering the alkylene oxide absorber is converted in the alkylene oxide absorber.

The gas composition from step (b) that is supplied to the alkylene oxide absorber comprises carbon dioxide. It is possible that the gas composition may contain insufficient carbon dioxide to achieve desired levels of carboxylation. This is likely to be the case when using a fresh batch of catalyst in step (a). An additional source of carbon dioxide is preferably supplied to the alkylene oxide absorber, e.g. carbon dioxide from a carbon dioxide recovery unit or, at start-up, carbon dioxide from an external source. The molar ratio of the total amount of carbon dioxide supplied to the alkylene oxide absorber to the amount of alkylene oxide supplied to the alkylene oxide absorber is preferably between 5:1 and 1:3, more preferably between 3:1 and 4:5. A higher quantity of carbon dioxide improves conversion to alkylene carbonate. However, a higher quantity of carbon dioxide also requires either additional removal capacity for carbon dioxide in the process, which can be costly, or operating the alkylene oxide catalyst at higher carbon dioxide concentration which adversely affects the alkylene oxide catalyst performance.

Gases that are not absorbed in the alkylene oxide absorber are preferably partially or entirely supplied to a carbon dioxide absorption column wherein the carbon dioxide is at least partially absorbed by a recirculating absorbent stream. Gases that are not absorbed by the recirculating absorbent stream are preferably recombined with any gases bypassing the carbon dioxide absorption column and are recycled to the alkylene oxide reactor. Because the process of the present invention achieves significant reaction of alkylene oxide and carbon dioxide in the alkylene oxide absorber, carbon dioxide is effectively captured in the alkylene oxide absorber, so the quantity of carbon dioxide in the gases leaving the alkylene oxide absorber is low, reducing the need for carbon dioxide removal apparatus. In one embodiment of the invention, the amount of carbon dioxide leaving the alkylene oxide absorber in a gas stream is sufficiently low that there is no requirement for a carbon dioxide absorption column for recovery of carbon dioxide.

Fat absorbent is withdrawn from the alkylene oxide absorber, preferably by withdrawing liquid from the bottom of the alkylene oxide absorber.

In one embodiment of the invention, a portion or all of the fat absorbent from step (c) is supplied to one or more finishing reactors before it is supplied to the one or more hydrolysis reactors in step (d). Supply to one or more finishing reactors is preferred if a significant quantity (e.g. at least 1%) of alkylene oxide supplied to the alkylene oxide absorber is not converted to alkylene carbonate in the alkylene oxide absorber. Conversely, if the majority (e.g. greater than 90%) of alkylene oxide supplied to the alkylene oxide absorber is converted to alkylene carbonate in the alkylene oxide absorber, then one or more finishing reactors may not be required and the equipment used in the process is thereby reduced. (The decision whether to employ one or more finishing reactors is most difficult in the region where from 90 to 99% of alkylene oxide supplied to the alkylene oxide absorber is converted to alkylene carbonate in the alkylene oxide absorber. In this range, a number of different factors, including costs and product quality requirements, are likely to be considered by the skilled person when considering whether to use one or more finishing reactors.) To maximise conversion of alkylene oxide in the alkylene oxide absorber, spraying nozzles can be employed in the bottom section of the alkylene oxide absorber, to disperse carbon dioxide and promote carboxylation. The one or more finishing reactors preferably include a plug flow reactor. In the one or more finishing reactors, further carboxylation of alkylene oxide occurs and preferably at least 50 wt % of alkylene oxide entering the finishing reactor is converted to alkylene carbonate in the finishing reactor, more preferably at least 90 wt %, most preferably at least 95%. The finishing reactor contains carboxylation catalyst. If a homogeneous catalyst is used in the alkylene oxide absorber, then the fat absorbent will comprise carboxylation catalyst and there is no requirement to add additional catalyst to the finishing reactor. However, in the embodiment wherein a heterogeneous catalyst is used in the alkylene oxide absorber it is preferred to incorporate a bed of heterogeneous catalyst in the finishing reactor, most preferably the same catalyst as is used in the absorber. Preferably additional carbon dioxide is supplied to the finishing reactor or to the fat absorbent after it has been withdrawn from the alkylene oxide absorber and before it is supplied to the finishing reactor.

A portion of the fat absorbent from step (c) and from any additional finishing reactors is supplied to one or more hydrolysis reactors. Preferably 1-50 wt % of the fat absorbent is supplied to the hydrolysis reactor, most preferably 2-20 wt % is supplied to the hydrolysis reactor. Preferably the remainder of the fat absorbent is recycled to the alkylene oxide absorber as the lean absorbent. If there is more than one hydrolysis reactor it is preferred that the hydrolysis reactors are connected in series, i.e. the portion of fat absorbent must pass through each hydrolysis reactor sequentially.

The fat absorbent that results from step (c) and from any additional finishing reactors must be split into at least two portions before any of the fat absorbent is supplied to the one or more hydrolysis reactors in step (d). Additionally the fat absorbent may undergo removal of light ends and/or removal of a homogeneous carboxylation catalyst before it is supplied to the one or more hydrolysis reactors. (Light ends are gases such as the alkene, and also ballast gases such as methane, that are present in the gas composition resulting from (a), are absorbed into the absorbent in step (c) and are therefore present in the fat absorbent.)

In a preferred method that can be used to accomplish splitting of the fat absorbent into two portions, removal of light ends and removal of a homogeneous carboxylation catalyst, the fat absorbent is supplied to a flash vessel. The flash vessel can be at a pressure from 0.01 to 2 MPa, preferably from 0.1 to 1 MPa, most preferably from 0.1 to 0.5 MPa. Light ends removed using the flash vessel are preferably recirculated to the alkylene oxide absorber, and may be supplied to the bottom of the alkylene oxide absorber. Recirculating the light ends to the alkylene oxide absorber increases the efficiency of the process because light ends, comprising alkene, are recovered and are not lost when carbon dioxide is removed from the process in a carbon dioxide bleed stream. A portion of the alkylene carbonate in the fat absorbent is flashed, subsequently condensed, and supplied to the one or more hydrolysis reactors. Remaining fat absorbent, which may contain homogeneous carboxylation catalyst is preferably recycled to the alkylene oxide absorber as the lean absorbent.

In an alternative method that can be used to accomplish splitting of the fat absorbent into a portion to be supplied to the one or more hydrolysis reactors and another portion (that is preferably recycled to the alkylene oxide absorber), the fat absorbent undergoes a liquid phase splitting. With this method, there is no removal of light ends with catalyst separation, so light ends are sent to the hydrolysis reactor as part of the fat absorbent. In this method, light ends are preferably removed from the hydrolysis reactor and are recycled to the alkylene oxide absorber.

In a yet further method, the light ends are removed using a flash vessel and preferably recycled, and the remaining fat absorbent subsequently undergoes a liquid phase splitting.

Water is supplied to the one or more hydrolysis reactors. The molar ratio of water to alkylene carbonate entering the reactor is preferably in the range of 2:1 to 1:2, most preferably about 1:1. If there is more than one hydrolysis reactor, water can be supplied directly to the first hydrolysis reactor only (so water is supplied to the subsequent hydrolysis reactors via the first hydrolysis reactor), or alternatively water can be supplied directly to the first hydrolysis reactor and to one or more subsequent hydrolysis reactors. The water is preferably supplied as steam.

The fat absorbent is contacted with water in the presence of one or more hydrolysis catalysts. In one embodiment, the one or more hydrolysis catalysts are homogeneous catalysts that are supplied to the one or more hydrolysis reactors. Homogeneous catalysts that are known to promote hydrolysis include basic alkali metal salts such as potassium carbonate, potassium hydroxide and potassium bicarbonate, or alkali metal metalates such as potassium molybdate. In another embodiment, the one or more hydrolysis catalysts are heterogeneous catalysts and are preferably contained in a fixed bed in the one or more hydrolysis reactors. Heterogeneous catalysts that promote hydrolysis include metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

In one embodiment of the invention, at least one of the one or more hydrolysis reactors is a baffled reactor, wherein the baffled reactor has at least four compartments, the compartments are formed by internal baffles and the internal baffles provide a sinuous route for reaction fluid through the reactor. Optionally steam is injected into the baffled reactor.

Carbon dioxide will be produced in the one or more hydrolysis reactors and is preferably separated from the product stream as it leaves the one or more hydrolysis reactors and at least partially recycled to the alkylene oxide absorber and/or to one or more finishing reactors.

The temperature in the one or more hydrolysis reactors is typically from 80 to 200° C., preferably from 100 to 180° C. The pressure in the one or more hydrolysis reactors is typically from 0.1 to 3 MPa. Higher pressure can enable recycling of carbon dioxide to the absorption column and finishing reactor without the need for compression.

The product stream from step (d) is supplied to a dehydrator. The stream that is supplied to the dehydrator preferably comprises very little alkylene oxide or alkylene carbonate, i.e. most of the alkylene oxide or alkylene carbonate has been converted to alkylene glycol prior to supply to the dehydrator column. Preferably the molar ratio of alkylene glycol to alkylene oxide and alkylene carbonate (combined) in the stream supplied to the dehydrator column is greater than 90:10, more preferably greater than 95:5, most preferably greater than 99:1. The dehydrator is preferably one or more columns, including at least one vacuum column, preferably operating at a pressure of less than 0.05 MPa, more preferably less than 0.025 MPa and most preferably about 0.0125 MPa.

If one or more homogeneous hydrolysis catalyst(s) are used in the one or more hydrolysis reactors, or if one or more homogeneous carboxylation catalyst(s) are used in the alkylene oxide absorber and not separated from the fat absorbent prior to supply to the one or more hydrolysis reactors, then the homogeneous catalyst(s) may be removed from the product stream from step (d) or alternatively from the dehydrated product stream from step (e). In one embodiment, the product stream from step (d) is supplied to a flash vessel to separate the homogeneous catalyst(s) (which are preferably recycled to the alkylene oxide absorber or to the one or more hydrolysis reactors) and is subsequently supplied to a dehydrator. In another embodiment, the dehydrated product stream from step (e) is supplied to a flash vessel to separate the homogeneous catalyst(s) (which are preferably recycled to the alkylene oxide absorber or to the one or more hydrolysis reactors) and then is subsequently purified to remove impurities.

The dehydrated product stream from step (e) is purified to remove impurities and provide a purified alkylene glycol product stream.

Figure 1:
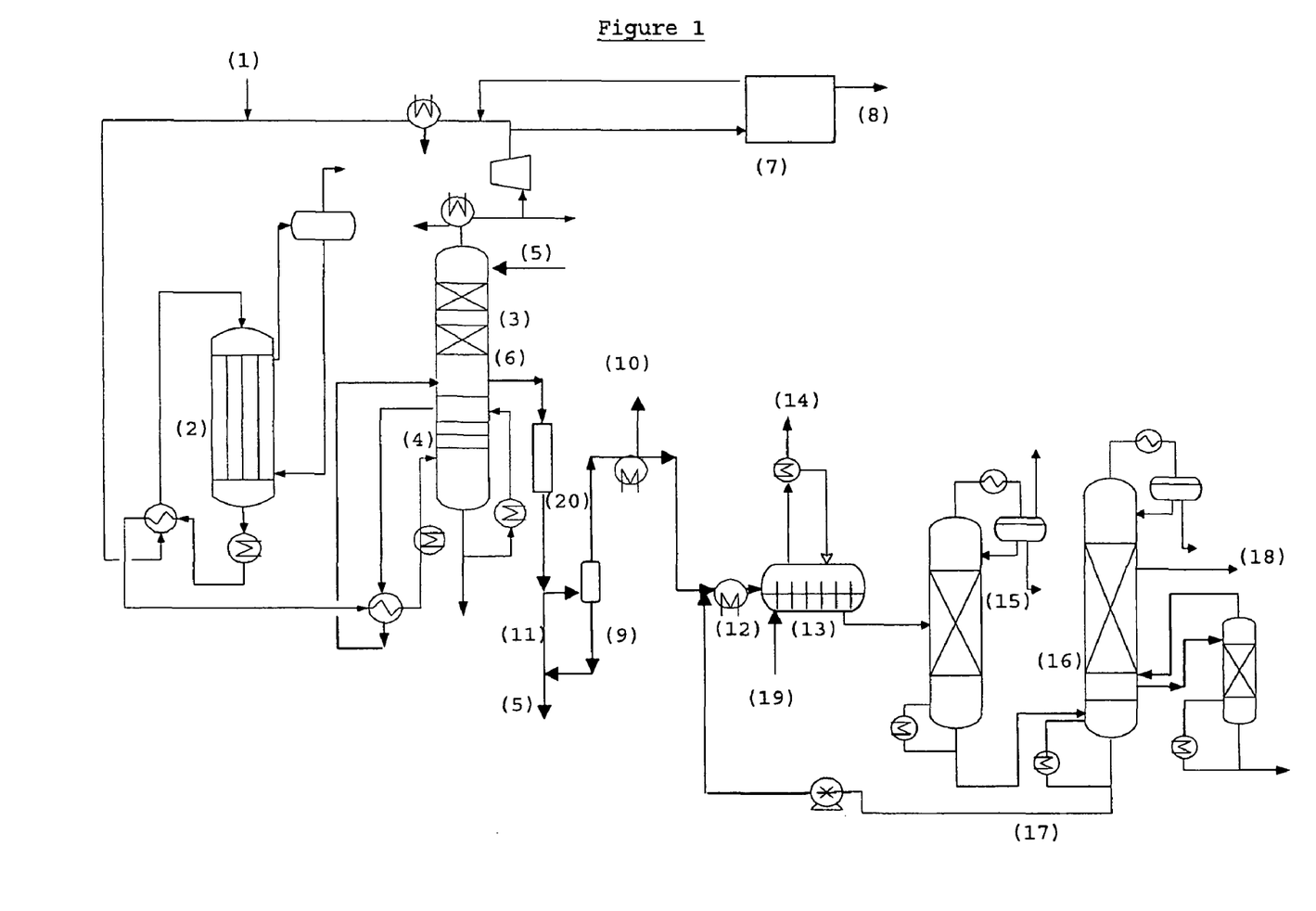
FIG. 1 is a schematic diagram showing a process according to an embodiment of the invention.

FIG. 1 shows a preferred embodiment of the process of the invention. Ethylene, oxygen, methane and moderator (e.g. monochloroethane) are supplied to the recycle gas at (1). In the ethylene oxide reactor (2), the ethylene and oxygen react, providing a gas composition comprising ethylene, oxygen, methane, ethylene oxide, moderator and carbon dioxide, which is cooled and supplied to the quench (4), below the bottom tray of the quench section. The quenched gas is reheated and fed to the ethylene oxide absorber column (3) below the bottom tray or below the packing material. Optionally, additional carbon dioxide from the carbon dioxide recovery section (7) or hydrolysis reactor (13) may also be supplied to the ethylene oxide absorber (3) or may be mixed with the gases before supply to the ethylene oxide absorber. Lean absorbent comprising greater than 70 wt % ethylene carbonate, less than 2 wt % water and a homogeneous carboxylation catalyst are supplied (5) at the top of the ethylene oxide absorber column (3). The lean absorbent is supplied at a temperature of 90° C. In the ethylene oxide absorber, ethylene oxide and carbon dioxide are absorbed into the lean absorbent and react to provide ethylene carbonate. The gases that are not absorbed in ethylene oxide absorber (3) are partially or entirely supplied to carbon dioxide recovery section (7) where carbon dioxide is removed from the gas. The recovered carbon dioxide stream (8) can partially or entirely be recirculated to the ethylene oxide absorber (3), directly or by mixing with the gas feed. The gas from the ethylene oxide absorber (3), the gas from carbon dioxide recovery section (7) and the recombined gas stream fed to the reactor (2) can be cooled to reduce the water content. The liquid knocked out of the gas stream can optionally be recirculated to the ethylene oxide absorber column (3).

Fat absorbent is withdrawn (6) from the ethylene oxide absorber bottom and is supplied to a finishing reactor (20). The fat absorbent stream is then split (11) and one portion is supplied to a flash vessel (9). The homogeneous carboxylation catalyst is separated in the flash vessel, is withdrawn from the flash vessel, and is combined with the portion of fat absorbent that was not supplied to the flash vessel, before being recirculated to the absorber as the lean absorbent (5). A light ends stream (10) is withdrawn after the flash vessel and can be recirculated to the ethylene oxide absorber (3) directly or by mixing with the gas feed. The fat absorbent stream is fed to heat exchanger (12) and is subsequently supplied to a hydrolysis reactor (13).

Steam (19) and homogeneous hydrolysis catalyst (17) are supplied to the hydrolysis reactor (13). In the hydrolysis reactor (13), ethylene carbonate and water react to give monoethylene glycol. The carbon dioxide gas released (14) can be recycled to the ethylene oxide absorber (3) directly, or by mixing with the ethylene oxide absorber feed, or can be totally or partially bled. The product stream from the hydrolysis reactor (13) is supplied to a dehydrator (15) where water is removed. The dehydrated product stream is withdrawn from the dehydrator (15) and supplied to the monoethylene glycol (MEG) purification column (16). A solution comprising the hydrolysis catalyst dissolved in glycols (17) is withdrawn from the bottom of the MEG purification column (16) and is recycled to the hydrolysis reactor (13). Monoethylene glycol product (18) is withdrawn from the MEG purification column top section.

Figure 2:
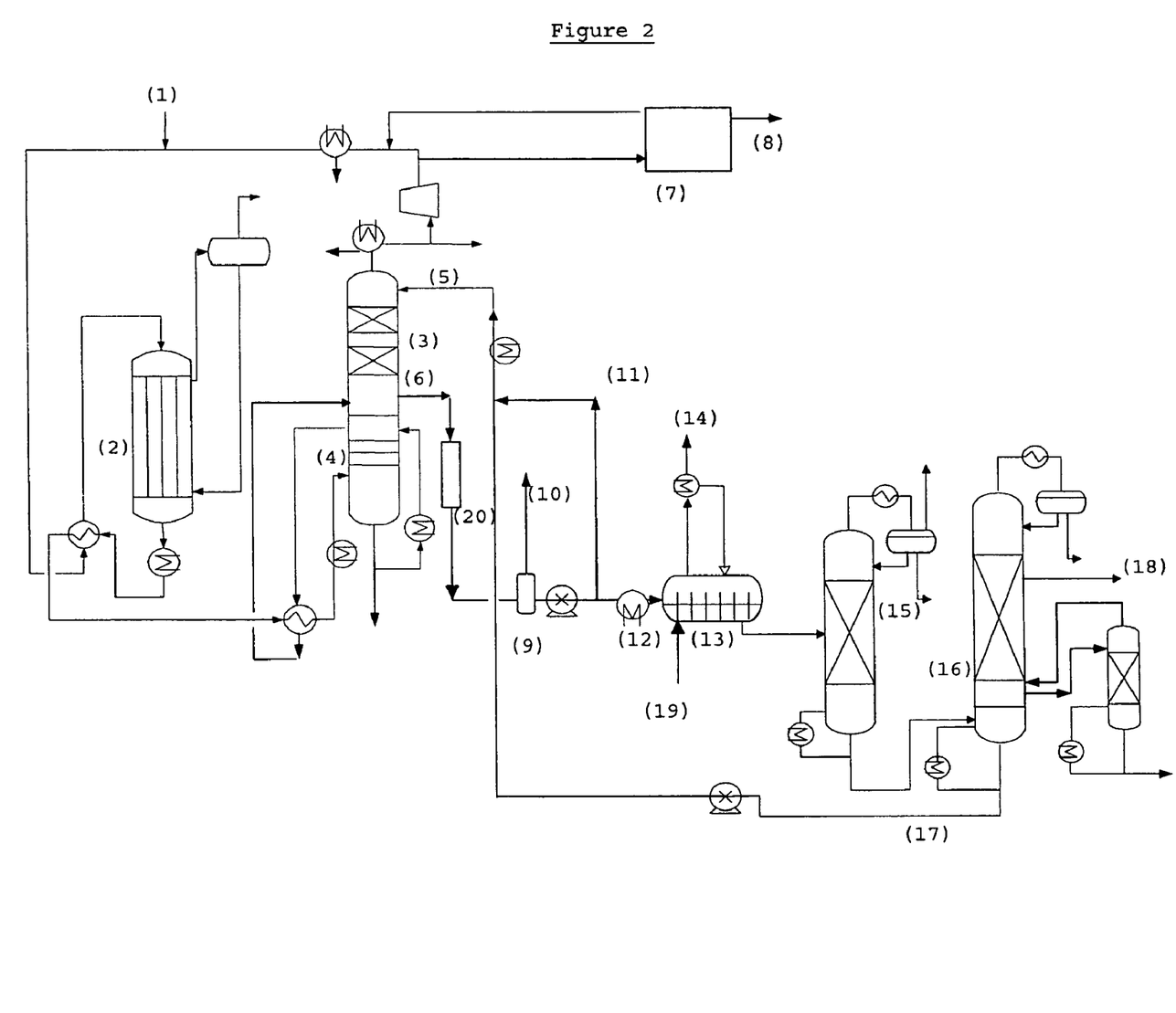
FIG. 2 is a schematic diagram showing a process according to another embodiment of the invention.

FIG. 2 shows an alternative preferred embodiment of the process of the invention wherein homogeneous carboxylation and hydrolysis catalysts are both present in the lean absorbent (5) that is supplied to the ethylene oxide absorber (3). The fat absorbent stream from the ethylene oxide absorber (3) is supplied to a finishing reactor (20) and then to a flash vessel (9). After the flash vessel the stream is split and one portion is fed to a heat exchanger (12) and is subsequently supplied to a hydrolysis reactor (13). The homogeneous catalysts are not separated in the flash vessel and remain in the fat absorbent that is supplied to the hydrolysis reactor. A solution comprising the carboxylation and hydrolysis catalysts dissolved in glycols (17) is withdrawn from the bottom of the MEG purification column (16) and is recycled to the ethylene oxide absorber (3) as lean absorbent (5) after mixing with the absorbent flow that is not supplied to the finishing reactor (11).

Figure 3:
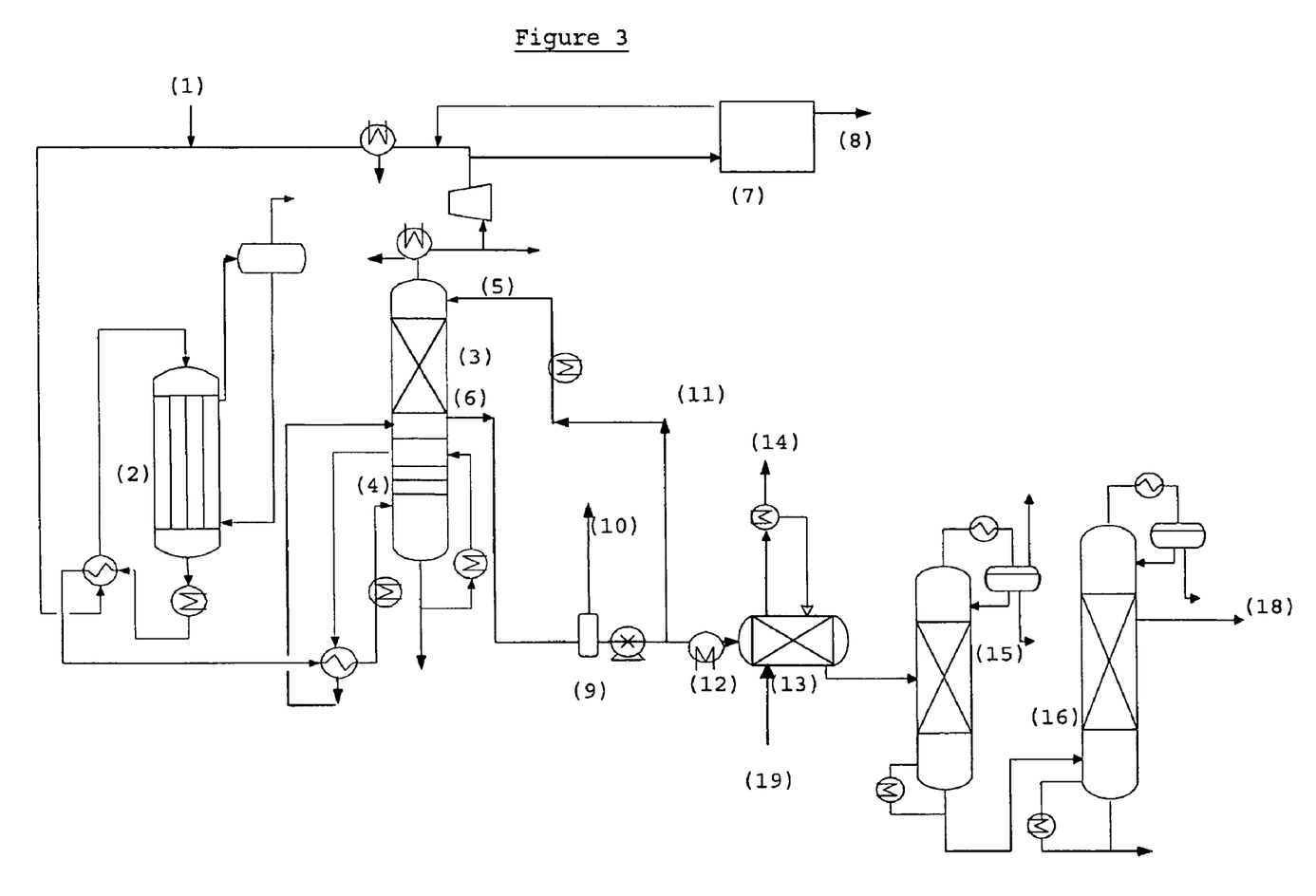
FIG. 3 is a schematic diagram showing a process according to another embodiment of the invention.

FIG. 3 shows yet another preferred embodiment of the process comprising a heterogeneous catalyst packing in the ethylene oxide absorber column (3) as well as a heterogeneous catalyst bed in the hydrolysis reactor (13). In this embodiment there is no requirement for catalyst separation or recirculation. No finishing reactor is used in this embodiment.

Figure 4:
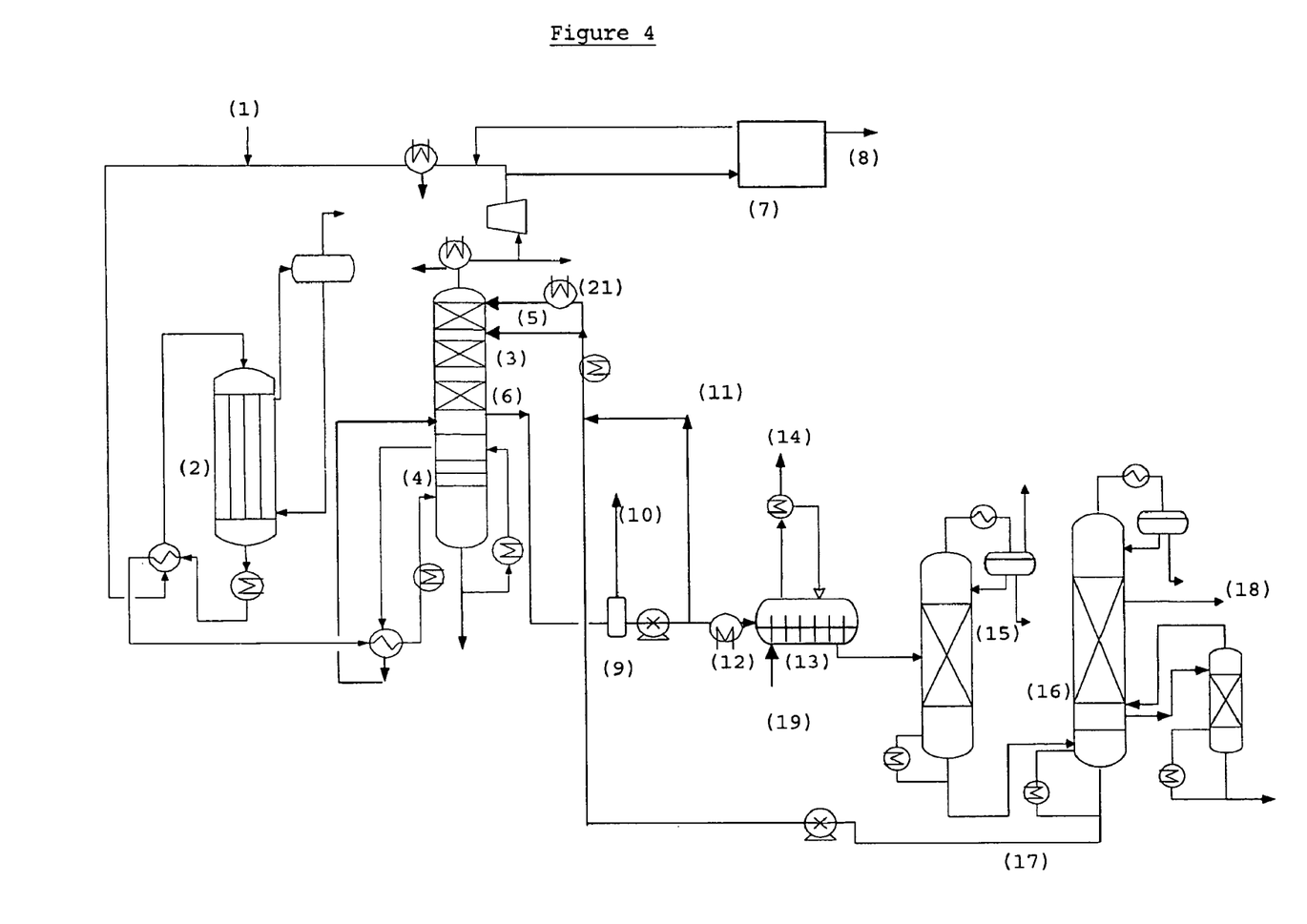
FIG. 4 is a schematic diagram showing a process according to another embodiment of the invention.

FIG. 4 shows an embodiment using homogeneous catalysts, where a portion of the lean absorbent is cooled in a heat exchanger (21) and is supplied to the ethylene oxide absorber column (3) above the top packing or top trays to absorb remaining ethylene oxide and/or contaminants in the top of the ethylene oxide absorber (3). No finishing reactor is used in this embodiment.

Figure 5:
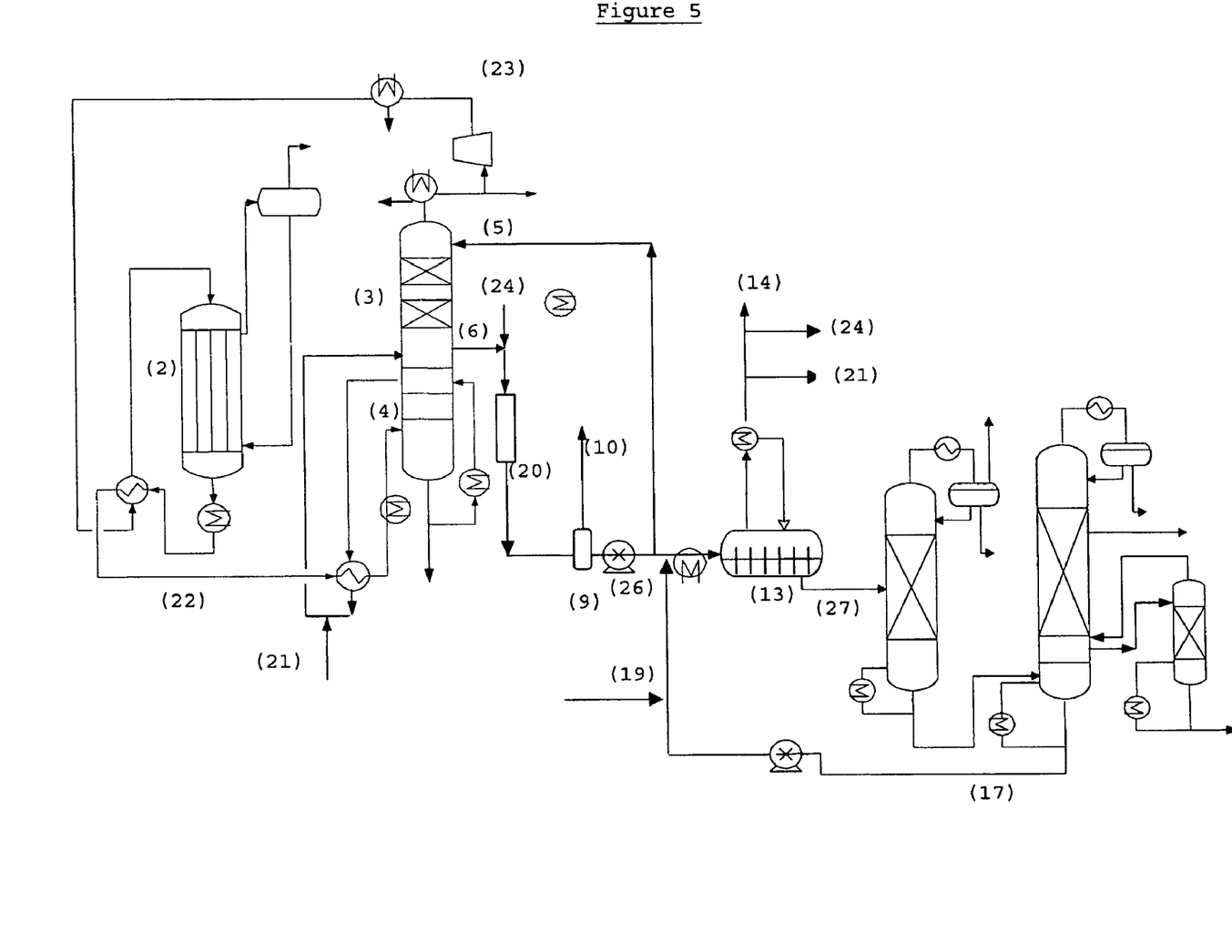
FIG. 5 is a schematic diagram showing a process according to another embodiment of the invention.

FIG. 5 shows an embodiment of the process using a heterogeneous catalyst packing in the ethylene oxide absorber column (3) and a homogeneous catalyst in the hydrolysis reactor (13). In this embodiment, the carbon dioxide content of the gases (23) leaving the ethylene oxide absorber (3) is sufficiently low that there is no requirement to recover carbon dioxide from this gas stream.

Figure 6:
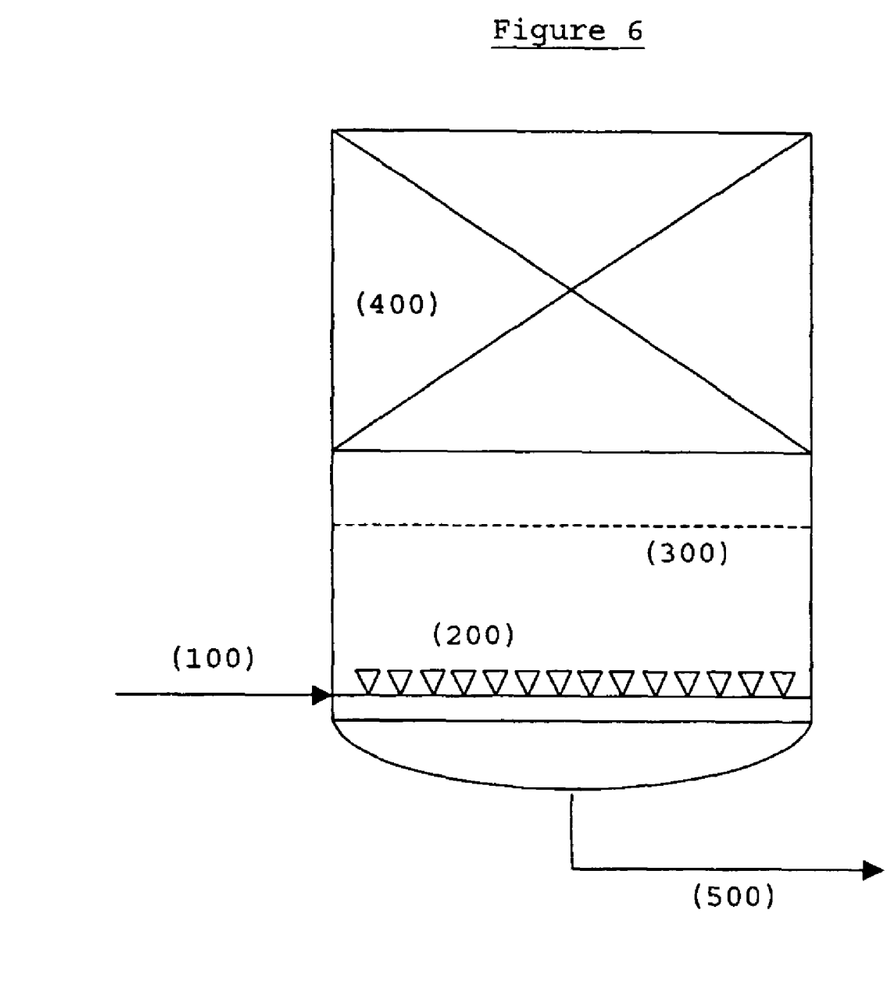
FIG. 6 is a schematic diagram showing an embodiment of the bottom of the alkylene oxide absorber column.

FIG. 6 describes an embodiment of the bottom of the ethylene oxide absorber column, where carbon dioxide gas (100) is supplied to the liquid though nozzles (200). The liquid level (300) is maintained well below the bottom tray or below the bottom of the column packing (400). Fat absorbent (500) leaves at the bottom.

The invention will now be described by reference to an example which is not intended to be limiting of the invention.

Example

The process of the invention was modelled, based upon a system as shown in FIG. 5. The production capacity of the ethylene oxide reactor is 1477 kmole/h. Product gasflow (22) from the ethylene oxide reactor (2) outlet is cooled from 245° C. in 3 steps to 50° C. and fed to a quench section (4) where water is removed by quenching with a circulating water stream of 1000 t/h cooled to 25° C., thereby reducing the ethylene oxide product gas water content from 1.1 mole % in the ethylene oxide reactor outlet to 0.3 mole % in the feed to the ethylene oxide absorber column (3). Thus, in the quench section 420 kmol/h water is removed and bled. With the quench bleed stream also 13 kmole/h ethylene oxide is bled. The quench section is modelled as an absorption section consisting of two theoretical stages integrated in the bottom of the same vessel as the ethylene oxide absorber column (3).

The gas leaving the quench section is reheated against ethylene oxide reactor product gas to a temperature of 92° C. A carbon dioxide stream of 500 kmole/h is recycled (21) from the hydrolysis reactor (13) and combined with the reheated gas from the quench. The reheated gas from the quench is fed to the bottom of the ethylene oxide absorption column (3). The column is filled with catalytic heterogeneous packing material, zinc iodide on Lewatit™ KR ion exchange resin in bromide form. The column operates at a top pressure of 22.5 bar and a pressure drop of 100 mbar. The column is modelled by 22 theoretical stages. Lean absorbent (5), with a temperature of 90° C., enters the same column at the top. The lean absorbent stream is 12286 kmole/h.

In the column, ethylene oxide (EO) and carbon dioxide will react to form ethylene carbonate. The Arrhenius type reaction rate equation is:

$$d[EO]/dt = -1.81E+10 * \exp\{-9264/T\} * [EO]$$

For the activity of the heterogeneous carboxylation catalyst it is essential to keep the water concentration as low as possible. Hydrolysis catalyst, an Amberjet 4200 resin in bicarbonate form, is mixed with the carboxylation catalyst in a ratio 1:10. Thus, the small amount of water entering the absorbent with the gas will react with ethylene oxide (EO) to monoethylene glycol, according to reaction equation:

$$d[EO]/dt = -2.0E+11 * \exp\{-9021/T\} * [EO] * [H_2O]$$

Table 1 below gives the resulting molar balance (mole flow in kmole/hr) for the ethylene oxide absorption column:

TABLE 1

|  | Gas in (21) + (22) | Absorbent in (5) | Gas out (23) | Absorbent Out (6) |
|---|---|---|---|---|
| Ethylene oxide | 1464 | 0 | 0.0039 | 116 |
| Water | 171 | 0 | 0 | 10 |
| Monoethylene glycol | 0 | 1433 | 5 | 1594 |
| Diethylene glycol | 0 | 0 | 0 | 0 |
| Ethylene Carbonate | 0 | 10838 | 9 | 12034 |
| Argon | 1789 | 0 | 1787 | 1 |
| Oxygen | 3183 | 0 | 3181 | 1 |
| Methane | 33861 | 2 | 33734 | 65 |
| Ethylene | 12369 | 8 | 12235 | 72 |
| Ethane | 503 | 0 | 502 | 1 |
| Carbon Dioxide | 1537 | 5 | 348 | 6 |

Carboxylation of ethylene oxide to ethylene carbonate is an exothermic reaction. A total of 20.6 MW of heat is removed from the column by means of two partial side draw-offs in the bottom section of the column. The drawn-off liquid is cooled to 95° C. and recycled to the column slightly below the draw-off point.

The gas leaving the top of the ethylene oxide absorber column (23) has a low concentration of carbon dioxide and water. Therefore no further treatment to remove carbon dioxide and water is needed in this example before the gas is recycled to the ethylene oxide reactor inlet. By cooling and knocking out the liquid, monoethylene glycol is removed from gas stream.

From column 5 in Table 1 it is clear that absorbent stream (6) leaving the column still contains unconverted ethylene oxide. The conversion of ethylene oxide fed to the ethylene oxide absorber column is 92%. Full conversion of ethylene oxide is achieved by treating the ethylene oxide absorption column product in a finishing reactor (20), which is an isothermal plug flow reactor packed with the same heterogeneous catalyst and with a liquid residence time of 11 seconds. The reactor is operated at 110° C. An additional amount of 159 kmole/h of carbon dioxide is fed to the finishing reactor to enable full conversion of ethylene oxide to ethylene carbonate.

A molar balance (mole flow in kmol/hr) of the finishing reactor is given in table 2:

TABLE 2

| | Absorbent In (6) | Carbon dioxide in (24) | Finishing Reactor out (25) |
|---|---|---|---|
| Ethylene oxide | 116 | 0 | 0 |
| Water | 10 | 0 | 0 |
| Monoethylene glycol | 1594 | 0 | 1604 |
| Diethylene glycol | 0 | 0 | 0 |
| Ethylene Carbonate | 12034 | 0 | 12140 |
| Argon | 1 | 0 | 1 |
| Oxygen | 1 | 0 | 1 |
| Methane | 65 | 0 | 65 |
| Ethylene | 72 | 0 | 72 |
| Ethane | 1 | 0 | 1 |
| Carbon Dioxide | 6 | 159 | 59 |

Liquid ethylene carbonate absorbs hydrocarbon gases such as methane and ethylene from the ethylene oxide reactor recycle gasflow. To avoid loosing valuable hydrocarbons like ethylene with the carbon dioxide bleed (14), the finishing reactor product is flashed. The pressure is reduced from 21.6 barg at the finishing reactor outlet to 1 barg in an adiabatic flash vessel (9). The molar balance (mole flow in kmol/hr) in table 3 shows that the majority of the ethylene and ethane is removed from the liquid absorbent and can be recycled to the ethylene oxide absorber column or recycle gas after compression.

TABLE 3

| | Absorbent In (25) | Light Ends Out (10) | Liquid out (26) |
|---|---|---|---|
| Ethylene oxide | 0 | 0 | 0 |
| Water | 0 | 0 | 0 |
| Monoethylene glycol | 1604 | 1 | 1603 |
| Diethylene glycol | 0 | 0 | 0 |
| Ethylene Carbonate | 12140 | 3 | 12137 |
| Argon | 1 | 1 | 0 |
| Oxygen | 1 | 1 | 0 |
| Methane | 65 | 62 | 3 |
| Ethylene | 72 | 63 | 9 |
| Ethane | 1 | 0 | 0 |
| Carbon Dioxide | 59 | 54 | 6 |

The major part of the liquid is pumped back as recycle flow (5) to the top of the ethylene oxide absorber, after being cooled to 95° C.

A minor part of the liquid is separated from the recycle stream, mixed with 1800 kmole/h water and the catalyst recycle of 200 kmole/h potassium carbonate dissolved in 3000 kmole/h monoethylene glycol. That solution is heated to 150° C. and fed to hydrolysis reactor (13). The hydrolysis reactor is a baffled vessel modelled as an isothermal plugflow reactor with a liquid residence time of 6 minutes, operated at 150° C. Carbon dioxide gas is released and can be partly recycled to the ethylene oxide reactor product gas (21) stream and the finishing reactor (24). Since the hydrolysis reactor is operated at 25 barg this can be done without the need of compression. The remaining carbon dioxide is vented to atmosphere (14).

The reaction rates used in the model are:

Ethylene carbonate+$H_2O$→Monoethylene glycol+ $CO_2$ $d[EC]/dt = -0.01*[EC]*[H_2O]$ Ethylene carbonate+Monoethylene glycol→Diethylene glycol+$CO_2$ $d[EC]/dt = -0.00001*[EC]*[MEG]$ The molar balance (mole flow in kmol/hr) for the hydrolysis reactor is given in table 4:

TABLE 4

| | Absorbent In (17) + (19) | Gas Out (14) + (21) + (24) | Reactor product (27) |
|---|---|---|---|
| Ethylene oxide | 0 | 0 | 0 |
| Water | 1800 | 51 | 455 |
| Monoethylene glycol | 3171 | 8 | 4453 |
| Diethylene glycol | 0 | 0.00007 | 1.38 |
| Ethylene Carbonate | 1293 | 0.0003 | 0.1 |
| Argon | 0 | 0 | 0 |
| Oxygen | 0 | 0 | 0 |
| Methane | 0 | 0 | 0 |
| Ethylene | 1 | 1 | 0 |
| Ethane | 0 | 0 | 0 |
| Carbon Dioxide | 1 | 1275 | 19 |

The hydrolysis reactor product is dehydrated with conventional technology and the essentially water-free glycol product is sent to a monoethylene glycol purification column. In the bottom of monoethylene glycol purification column, monoethylene glycol is flashed to the top section of the column for purification and a solution of $K_2CO_3$ in monoethylene glycol (17) is recycled to inlet of the hydrolysis reactor.

What is claimed is:
1. A process for the preparation of an alkylene glycol from an alkene comprising steps of:
   (a) reacting the alkene with oxygen in the presence of a catalyst in a reactor to produce a gas composition comprising alkylene oxide, alkene, oxygen, carbon dioxide and water vapour;
   (b) removing water from the gas composition;
   (c) supplying the gas composition from (b) to an alkylene oxide absorber, supplying lean absorbent to the alkylene oxide absorber, contacting the gas composition with lean absorbent in the alkylene oxide absorber in the presence of one or more catalysts that promote carboxylation, and withdrawing fat absorbent from the absorber, wherein the lean absorbent comprises at least 50 wt % alkylene carbonate and comprises less than 10 wt % water, and wherein the lean absorbent is supplied at a temperature greater than 60° C. and wherein the temperature in the alkylene oxide absorber is controlled such that it is greater than 90° C.;
   (d) supplying a portion of the fat absorbent from step (c) to one or more hydrolysis reactors, supplying water to the one or more hydrolysis reactors, contacting the fat absorbent with water in the presence of one or more hydrolysis catalysts in the one or more hydrolysis reactors, and withdrawing a product stream from the one or more hydrolysis reactors;

(e) supplying the product stream from step (d) to a dehydrator, removing water and providing a dehydrated product stream; and (f) purifying the dehydrated product stream from step (e) and providing a purified alkylene glycol product stream.

2. A process according to claim 1, wherein in step (b), water is removed either by quenching, wherein the gas composition is contacted with a recirculating aqueous solution, and/or by cooling the gas composition using heat exchangers.

3. A process according to claim 1, wherein the alkylene oxide absorber comprises a column of vertically stacked trays or a packed column.

4. A process according to claim 1, wherein the temperature in the alkylene oxide absorber is controlled and such that it is less than 250° C.

5. A process according to claim 1, comprising supplying carbon dioxide to the alkylene oxide absorber from a carbon dioxide recovery unit and/or from an external source.

6. A process according to claim 1, comprising supplying a portion or all of the fat absorbent from step (c) to one or more finishing reactors in which further carboxylation of alkylene oxide occurs, before supplying the fat absorbent to the one or more hydrolysis reactors in step (d).

7. A process according to claim 1, comprising supplying 1-50 wt % of the fat absorbent from step (c) and from any additional finishing reactors to the hydrolysis reactor, and recycling the remaining 50-99 wt % of the fat absorbent to the alkylene oxide absorber as all or part of the lean absorbent.

8. A process according to claim 1, comprising supplying the fat absorbent from step (c) and from any additional finishing reactors to a flash vessel, removing light ends using the flash vessel and recirculating the light ends to the alkylene oxide absorber.

9. A process according to claim 1, wherein the lean absorbent comprises a homogeneous carboxylation catalyst, the process comprising supplying the fat absorbent from step (c) and from any additional finishing reactors to a flash vessel, withdrawing a mixture comprising homogeneous carboxylation catalyst and alkylene carbonate from the flash vessel, and recycling the mixture to the alkylene oxide absorber as a component of the lean absorbent.

10. A process according to claim 1, comprising supplying a homogeneous hydrolysis catalyst to the hydrolysis reactor, supplying the product stream from step (d) or the dehydrated product stream from step (e) to a flash vessel, withdrawing a mixture comprising homogeneous hydrolysis catalyst and alkylene glycol from the flash vessel, and recycling the mixture to the hydrolysis reactor.

11. A process according to claim 1, wherein the lean absorbent comprises a homogeneous carboxylation catalyst and a homogeneous hydrolysis catalyst, comprising supplying the product stream from step (d) or the dehydrated product stream from step (e) to a flash vessel to separate the homogeneous catalysts, and recycling the catalysts to the alkylene oxide absorber.

12. A process according to claim 1, wherein the one or more catalysts that promote carboxylation in the alkylene oxide absorber is/are heterogeneous, and the heterogeneous catalyst(s) are contained in vertically stacked trays or in the packing of a packed column.

13. A process according to claim 1, wherein at least 60% of the alkylene oxide entering the alkylene oxide absorber is converted to alkylene carbonate in the alkylene oxide absorber.

\* \* \* \* \*